United States Patent [19]

Meyer et al.

[11] 4,291,056
[45] Sep. 22, 1981

[54] PESTICIDAL ESTERS

[75] Inventors: Willy Meyer, Riehen; Jozef Drabek, Allschwil; Saleem Farooq, Aesch; Laurenz Gsell, Füllinsdorf; Friedrich Karrer, Zofingen, all of Switzerland

[73] Assignee: Ciba-Geigy Corporation, Ardsley, N.Y.

[21] Appl. No.: 707,136

[22] Filed: Jul. 20, 1976

[30] Foreign Application Priority Data

Jul. 28, 1975 [CH] Switzerland .................. 9859/75
Jun. 4, 1976 [CH] Switzerland .................. 7110/76

[51] Int. Cl.³ .............. A01N 53/00; C07C 69/743; C07C 121/75
[52] U.S. Cl. .............. 424/304; 260/465 D; 424/305; 560/124
[58] Field of Search .............. 260/465 D, 468 H; 424/304, 305

[56] References Cited

U.S. PATENT DOCUMENTS 3,979,519  9/1976  Punja .................. 424/304

Primary Examiner—Dolph H. Torrence
Attorney, Agent, or Firm—Frederick H. Rabin

[57] ABSTRACT 3-(2,2-Dichlorovinyloxy)-benzylesters of the formula

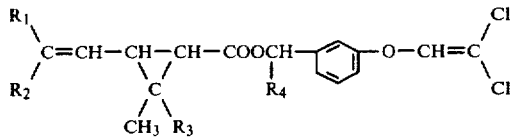

wherein each of
$R_1$ and $R_2$ independently represent fluoro, chloro, bromo or methyl,
$R_3$ represents hydrogen or methyl,
$R_4$ represents hydrogen or cyano, processes for their production and their use in pest control.

11 Claims, No Drawings

PESTICIDAL ESTERS

The present invention provides cyclopropanecarboxylic acid 3-(2,2-dichlorovinyloxy)benzyl esters, a process for their production and a method of using them in pest control.

The cyclopropanecarboxylic acid 3-(2,2-dichlorovinyloxy)benzyl esters have the formula

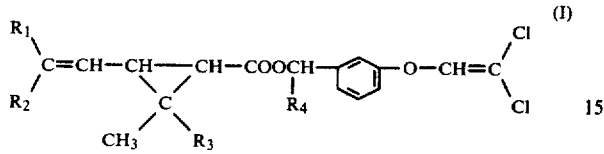
(I)

wherein each of $R_1$ and $R_2$ independently represents a fluorine, chlorine or bromine atom or a methyl group, $R_3$ represents a hydrogen atom or a methyl group, $R_4$ represents a hydrogen atom or a cyano group.

Particularly important compounds on account of their action are those of formula I, wherein $R_1$ and $R_2$ are the same and represent a fluorine, chlorine or bromine atom or a methyl group, $R_3$ represents a hydrogen atom or a methyl group, $R_4$ represents a hydrogen atom or a cyano group.

Preferred compounds are those of formula I, in which $R_1$ and $R_2$ are the same and represent a fluorine, chlorine or bromine atom or a methyl group, $R_3$ represents a methyl group and $R_4$ represents a cyano group.

Particularly preferred compounds are those of formula I, wherein $R_1$ and $R_2$ are the same and represent a fluorine, chlorine or bromine atom or a methyl group, $R_3$ represents a methyl group and $R_4$ represents a cyano group.

The compounds of formula I are obtained by known methods, for example

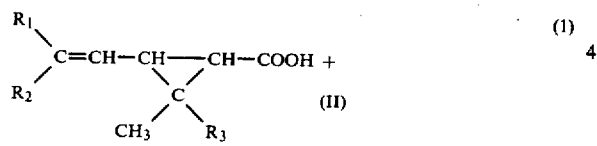
(1)

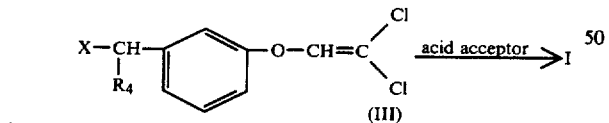
(2)

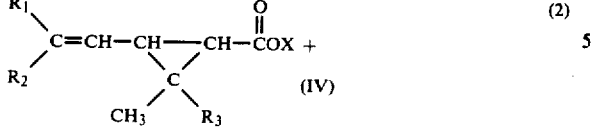
(3)

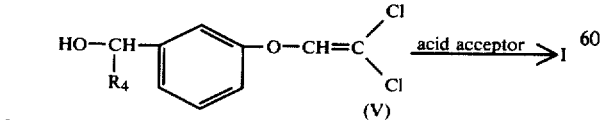

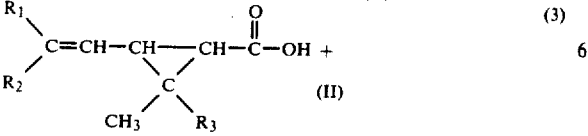

-continued

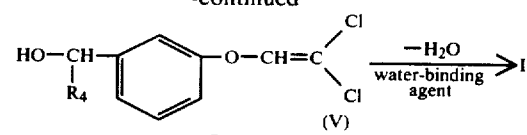

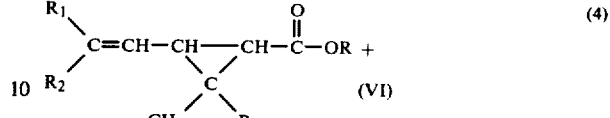
(4)

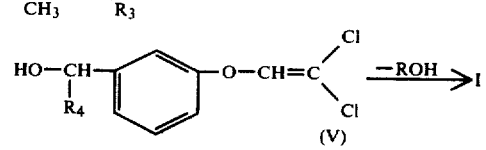

In the formulae II to VI, the symbols $R_1$ to $R_4$ have the same meanings as indicated for formula I, X represents halogen, particularly a chlorine or bromine atom and $R_4$ represents a $C_1$-$C_4$ alkyl group, especially a methyl or ethyl group.

Suitable acid acceptors for processes 1 and 2 are, in particular, tertiary amines, such as trialkylamines and pyridine; hydroxides, oxides, carbonates and bicarbonates of alkali metals and alkaline earth metals as well as alkali metal alcoholates, such as potassium t.-butylate and sodium methylate. Dicyclohexylcarbodiimide can be used for example as water-binding agent for process 3.

Processes 1 to 4 are carried out at a reaction temperature between $-10°$ and $+100°$ C., usually between 20° and 80° C., at normal or elevated pressure and preferably in an inert solvent or diluent.

Examples of suitable solvents or diluents are ethers, for example diethyl ether or dipropyl ether, or ethereal compounds, such as dioxane, dimethoxyethane or tetrahydrofurane; amides, such as N,N-dialkylated carboxylic acid amides; aliphatic, aromatic and halogenated hydrocarbons, especially benzene, toluene, xylene and chlorobenzenes; nitriles, such as acetonitrile, dimethyl sulfoxide and ketones, such as acetone and methyl ethyl ketone. Process 2 can also be performed in aqueous solution.

The starting materials of formulae II to VI are known or they can be produced by methods analogous to known ones.

A method for the preparation of the substance of formula II is described in Example 1.

The compounds of formula I are present as a mixture of the different optically active or cis-trans-isomers, unless they are prepared from optically active starting materials or pure cis- or trans-isomers. The various isomeric mixtures can be separated by known means into the pure isomers.

The compounds of formula I are to be understood as meaning the individual isomers as well as mixtures thereof.

Compounds of formula I are suitable for combating a variety of animal and vegetable pests.

Thus they can be used for combating representatives of phytopathogenic mites e.g. of the genera Tetranychus and Panonychus or of ecto-parasites of the families Dermanyssidae and Ixodidae.

Above all they are suitable for combating insects of the families Tettigoniidae, Gryllidae, Gryllotalpidae, Blattidae, Reduviidae, Pyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae and Pulicidae.

Above all, compounds of formula I are suitable for combating plant-damaging insects, in particular insects that damage ornamental and useful plants by eating, especially in cotton plantations (for example Spodoptera littoralis and Heliothis virescens), and in vegetable crops (for example Leptinotarsa decemlineata and Myzus persicae).

Active compounds of formula I also display a very good action on flies, for example Musca domestica and on mosquito larvae. The acaricidal and insecticidal action can be substantially broadened by the addition of other insecticides or acaricides and adapted to prevailing circumstances. Suitable additives are for example organic phosphorus compounds; nitrophenols and their derivatives; formamidines; ureas: pyrethroids, carbamates and chlorinated hydrocarbons.

With particular advantage the compounds of formula I are combined with substances which exert a synergistic or intensifying effect on pyrethroids. Examples of such compounds include piperonylbutoxide, propinyl ethers, N-propinyl oximes, propinyl carbamates, propinyl phosphonates, 2-(3,4-methylene-dioxyphenoxy-3,6,9-trioxaundecane(sesamex and/or sesoxane), S,S,S-tributylphosphorotrithioates, 1,2-methylenedioxy-4-(2-octylsulphonyl) propyl-benzene.

The compounds of formula I can be used as pure active substance or together with suitable carriers and/or additives. Suitable additives can be solid or liquid and correspond to the substances conventionally used in the art of formulation, such as natural or regenerated substances, solvents, dispersants, wetting agents, stickers, thickeners, binding agents and/or fertilizers.

The compositions of the present invention are obtained in known manner by intimately mixing and/or milling active compounds of formula I with suitable carriers, with or without the addition of dispersants or solvents which are inert to the active substances.

The active compounds can be in the form of and used in the following application forms:

Solids dusts, tracking agents, granulates (coated granulates, impregnated granulates and homogranulates);

Liquids (a) concentrates of active compounds which are dispersible in water: wettable powders, pastes, emulsions;
(b) solutions:

The content of active compounds in the formulations described above varies between 0.1 and 95%, in which connection it is to be mentioned that when the compounds are applied from an aircraft or by other suitable means of application, concentrations of up to 99.5% or even pure active compound can be used. The active compounds of formula I can for example be formulated as follows (parts denote parts by weight).

Dust (a)

5 parts of active compound,
95 parts of talcum.

(b)

2 parts of active compound,
1 part of highly dispersed silicic acid,
97 parts of talcum The active substances are mixed with the carriers and milled.

Granulate

For the preparation of a 5% granulate the following ingredients are used:
5 parts of active substance,
0.25 part of epichlorohydrine,
0.25 part of cetyl polyglycol ether,
3.50 parts of polyethylene glycol,
91 parts of kaolin (particle size 0.3 to 0.8 mm).

The active compound is mixed with epichlorohydrin and dissolved in 6 parts of acetone, then polyethylene glycol and cetyl polyglycol ether are added. The resultant solution is sprayed onto kaolin and the acetone is subsequently evaporated in vacuo.

Wettable powder

The following ingredients are used to prepare (a) a 40%, (b) and (c) a 25% and (d) a 10% wettable powder:

(a)

40 parts of active ingredient,
5 parts of sodium lignin sulphonate,
1 part of sodium dibutyl-naphthalene sulphonate,
54 parts of silicic acid;

(b)

25 parts of active compound,
4.5 parts of calcium lignin sulphonate,
1.9 parts of Champagne-chalk/hydroxyethylcellulose mixture (1:1),
1.5 parts of sodium dibutyl-naphthalenesulphonate,
19.5 parts of silicic acid,
19.5 parts of Champagne-chalk,
28.1 parts of kaolin;

(c)

25 parts of active compound
2.5 parts of isooctylphenoxy-polyethylene-ethanol,
1.7 parts of Champagne-chalk/hydroxyethylcellulose mixture (1:1),
8.3 parts of sodium aluminium silicate,
16.5 parts of infusorial earth,
46 parts of kaolin;

(d)

10 parts of active compound,
3 parts of a mixture of sodium salts of saturated fatty alcohol sulphonates,
5 parts of naphthalenesulphonic acid/formaldehyde condensate,
82 parts of kaolin.

The active compounds are intimately mixed with the additives in proper mixers and milled in suitable mills and rollers to yield wettable powders, which can be diluted with water to give suspensions of any required concentration.

Emulsifiable concentrates

The following substances are used to obtain (a) a 10%, (b) a 25%, (c) a 50% emulsifiable concentrate:

(a)

10 parts of active compound,
3.4 parts of epoxidized vegetable oil,
3.4 parts of a combination emulsifier, composed of fatty alcohol polyglycol ether and calcium alkylarylsulphonate,
40 parts of dimethyl formamide,
43.2 parts of xylene;

(b)

25 parts of active compound,
2.5 parts of epoxidized vegetable oil,
10 parts of an alkylarylsulphonate/fatty alcohol polyglycol ether mixture,
5 parts of dimethyl formamide
57.5 parts of xylene;

(c)

50 parts of active compound,
4.2 parts of tributylphenol polyglycol ether,
8.5 parts of calcium dodecylbenzenesulfonate,
20 parts of cyclohexanone,
20 parts of xylene.

Emulsions of any required concentration can be prepared by diluting the above described concentrates with water.

Spray

The following ingredients are used to obtain (a) a 5% and (b) a 95% spray:

(a)

5 parts of active compound,
1 part of epichlorohydrin,
94 parts of ligroin (boiling range 160°-190° C.);

(b)

95 parts of active compound,
5 parts of epichlorohydrin.

EXAMPLE 1

I. Preparation of 2,2-dimethyl-3-(1-isobutenyl)-cyclopropanecarboxylic acid 3-(2,2-dichlorovinyloxy)-benzyl ester.

(a) 3-(2,2,2-trichloro-1-acetoxy-ethoxy)-toluene

To a solution of 147 g of chloral hydrate and 54 g of m-cresol in 100 ml of trichloromethane are slowly added 111 g triethylamino while vigorously cooling and subsequently 78.5 g of ethyl chloride are added dropwise at a temperature of 0°-10° C. The reaction mixture is stirred at room temperature for 2 hours, then filtered, washed with water and concentrated. High-vacuum distillation yields 163 g of 3-(2,2,2,-trichloro-1-acetoxyethoxy-toluene with a boiling point of 100°-109° C./0.05 Torr.

(b) 3-(2,2-dichlorovinyloxy)-toluene 71 g of 3-(2,2,2-trichloro-1-acetoxy-ethoxy)-toluene and 150 ml of acetic acid are stirred in a reaction vessel at 35°-45° C. 37 g of zink dust are added subsequently in the course of 2 to 3 minutes and the resultant reaction mixture is stirred for 1 hour at room temperature. The suspension is then mixed with hexane, filtered and washed. Acetic acid is removed by shaking out the organic phase with 2 N NaOH. After evaporation, 43 g 3-(2,2-dichlorovinyloxy)-toluene are obtained as a colourless oil, which can be used for processing without purification.

(c) 3-(2,2-dichlorovinyloxy)-benzyl bromide 39 g of 3-(2,2-dichlorovinyloxy)-toluene and 34.5 g of N-bromosuccinimide are refluxed in 250 ml of carbon tetrachloride for 1 hour. 0.5 g of dibenzoyl peroxide is added and the mixture is refluxed for a further hour. Then succinimide is filtered off, the solution is totally concentrated and the residue distilled under a high vacuum, to yield 27 g of 3-(2,2-dichlorovinyloxy)-benzyl bromide as a colourless oil, which boils at 108°-109° C./0.1 Torr.

(d) 2,2-dimethyl-3-(1-isobutenyl)-cyclopropane carboxylic acid 3-(2,2-dichlorovinyloxy)-benzyl ester:

15.3 g of 3-(2,2-dichlorovinyloxy)-benzyl bromide, 11.0 g of 2,2-dimethyl-3-(1-isobutenyl)-cyclopropanecarboxylic acid and 9.5 g of potassium carbonate are refluxed for 5 hours in 100 ml of methyl ethyl ketone. Subsequently the methyl ethyl ketone is evaporated, the residue is dissolved in toluene and washed with NaOH/NaCl and then with water. After drying and evaporation 16.7 g of the desired product of the formula

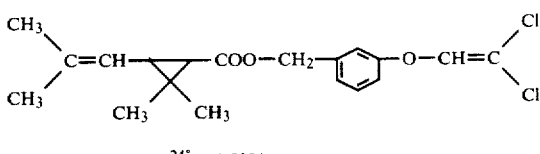

$n_D^{24°} = 1.5381$ is obtained.

II. Preparation of 2,2-dimethyl-3-(1-isobutenyl)-cyclopropanecarboxylic acid 3-(2,2-dichlorovinyloxy)-α-cyanobenzyl ester (a) 3-(2,2-dichlorovinyloxy)benzaldehyde To a solution of 8.5 g of 3-(2,2-dichlorovinyloxy)-benzyl bromide in 12.6 ml of acetic acid and 12.6 ml of water are added 8.4 g of hexamethylene tetramine. The resultant solution is refluxed for two hours. Subsequently 10 ml of HCl are added and the reaction mixture is stirred for half an hour at 100°-110° C. The solution is washed with 100 ml of water and extracted cold (3 times) with 100 ml of ethyl acetate. The extract is washed with sodium carbonate solution and evaporated, to yield 5.8 g of 3-(2,2-dichlorovinyloxy)-benzaldehyde as a yellowish-brown oil, which can be used without further purification.

(b) 3-(2,2-dichlorovinyloxy)mandelonitrile

To the combined solutions of 30 g of 3-(2,2-dichlorovinyloxy)benzaldehyde in 320 ml of ethanol and 15 g of NaCN in 30 ml water are added 39 ml of acetic acid dropwise at 0°-5° C. in the course of 1 hour. The resultant solution is stirred for 1 hour at 20°-25° C. and subsequently diluted with 1000 ml of H₂O. The product is extracted with toluene, washed and evaporated, to yield 31 g of 3-(2,2-dichlorovinyloxy)mandelonitrile. The crude product can be processed without further purification.

(c) 2,2-dimethyl-3-(1-isobutenyl)-cyclopropanecarboxylic acid 3-(2,2-dichlorovinyloxy)-α-cyanobenzyl ester To a solution of 9.8 g of 3-(2,2-dichlorovinyloxy)-mandelonitrile and 7.5 g of 2,2-dimethyl-3-(1-isobutenyl)-cyclopropanecarboxylic acid chloride in 100 cc toluene is added a solution of 3.5 g of pyridine in 200 ml toluene dropwise within 10 minutes. The resultant suspension is stirred for 15 hours at 20°-25° C., washed with dilute HCl and totally concentrated.

The crude product obtained is chromatographed with toluene on silica gel to yield 7.5 g of the compound of formula

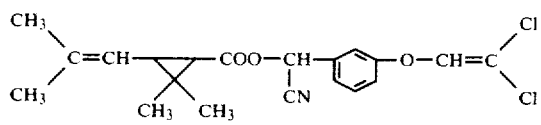

as a bluish-yellow liquid: $n_D^{22°} = 1.5360$.

The following compounds of formula I

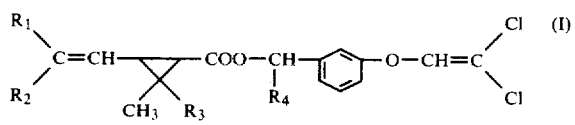

are obtained in analogous manner:

| R$_1$ | R$_2$ | R$_3$ | R$_4$ | physical data |
|---|---|---|---|---|
| Cl | Cl | CH$_3$ | H | $n_D^{22°} = 1.5545$ |
| Cl | Cl | CH$_3$ | CN | $n_D^{25°} = 1.5475$ |
| Cl | Cl | H | H | $n_D^{20°} = 1.5657$ |
| Cl | Cl | H | CN | $n_D^{20°} = 1.5585$ |
| Br | Br | CH$_3$ | H | $n_D^{20°} = 1.5693$ |
| Br | Br | CH$_3$ | CN | $n_D^{20°} = 1.5654$ |
| F | F | CH$_3$ | CN | $n_D^{20°} = 1.5210$ |

EXAMPLE 2

A. Insecticidal stomach poison action

Tobacco and potato plants were sprayed with a 0.05% aqueous active compound emulsion (obtained from a 10% emulsifiable concentrate). After the spray coating had dried, the tobacco and potato plants were populated with caterpillars of *Spodoptera littoralis* in the L$_3$-stage and of Heliothis virescens in the L$_3$-stage. The test was carried out at 24° C. and 60% relative humidity.

The compound of Example I showed in this test a positive stomach poison action on *Spodoptera littoralis* and *Heliothis virescens* caterpillars.

B. Insecticidal contact action

One day before applying the active compound, broad beans (Vicia faba), which have been cultivated in pots, were infected with about 200 aphids (*Aphis fabae*) per plant. A spray broth in an active compound concentration of 1000 ppm (prepared from a 25% wettable powder) was applied with a compressed air spraying apparatus to the leaves occupied by the aphids. The evaluation was performed 24 hours after the application. The compound of Example 1 displayed in this test good contact action on *Aphis fabae*.

EXAMPLE 3

Efficacy against ticks

A. *Rhipicephalus bursa*

5 Adult ticks or 50 tick larvae were counted into each of a number of test tubes and immersed for 1 to 2 minutes in 2 ml of an aqueous emulsion containing a concentration of 100, 10, 1, and 0.1 ppm of test compound respectively. Each tube was then sealed with a cotton wool plug and turned upside down to enable the cotton wool to absorb the active substance emulsion. The adults were evaluated after 2 weeks and the larvae after 2 days. Each test was repeated twice.

B *Boophilus microplus* (larvae)

20 OP-sensitive and 20 OP-resistent larvae were tested in aqueous emulsions analogous to those used in test A. (The resistance refers to the tolerance towards diazinone).

The compounds acted in these tests on adults and larvae of *Rhipicephalus bursa* as well as on sensitive and OP-resistant larvae of *Boophilus microplus*.

We claim:

1. A compound of the formula

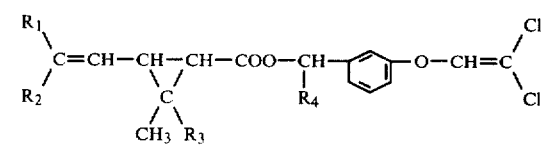

wherein R$_1$ and R$_2$ are the same and represents a fluorine, chlorine or bromine atom or a methyl group, R$_3$ represents a methyl group and R$_4$ represents a cyano group.

2. A compound according to claim 1 of formula

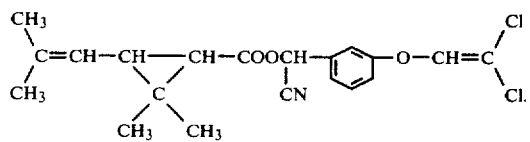

3. A compound according to claim 1 of formula

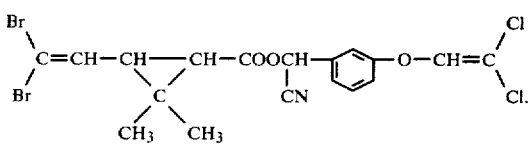

4. A compound according to claim 1 of formula

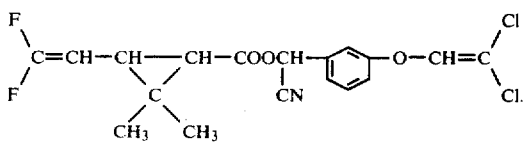

5. (±)-α-Cyano-3(2,2-dichlorovinyloxy)benzyl (±) cis/trans-2(2,2-dichlorovinyl)3,3-dimethylcyclopropane carboxylate.

6. An insecticidal and acaricidal composition comprising an insecticidally and acaricidally effective amount of a compound according to claim 1, together with a suitable carrier therefor.

7. A method for combatting insects and acarids which comprises applying to the locus thereof an insecticidally and acaricidally effective amount of a compound according to claim 1.

8. The method of claim 7, wherein said compound corresponds to the formula

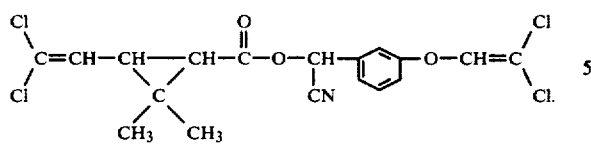
9. The method of claim 8, wherein said compound corresponds to the formula
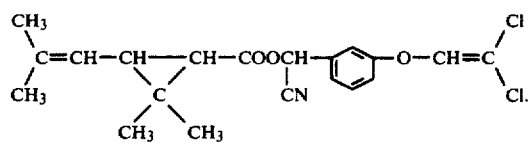
10. The method of claim 8, wherein said compound corresponds to the formula
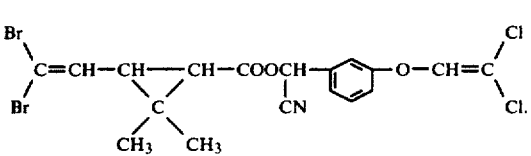
11. The method of claim 8, wherein said compound corresponds to the formula
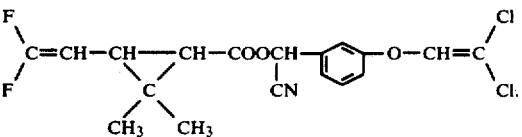
* * * * *